(12) United States Patent
Hsuan et al.

(10) Patent No.: US 9,470,685 B2
(45) Date of Patent: Oct. 18, 2016

(54) METHOD OF DISTINGUISHING MESENCHYMAL STEM CELLS

(71) Applicant: Meridigen Biotech Co., Ltd., Taipei (TW)

(72) Inventors: Chang-Yo Hsuan, Taipei (TW); Wei-Ting Liu, Taipei (TW); Shih-Pei Shen, Taipei (TW); Yun Lin, Taipei (TW); Yuan-Tsung Li, Taipei (TW); Chia-Chi Chang, Taipei (TW)

(73) Assignee: MERIDIGEN BIOTECH CO., LTD., Taipei (TW)

( * ) Notice: Subject to any disclaimer, the term of this patent is extended or adjusted under 35 U.S.C. 154(b) by 18 days.

(21) Appl. No.: 14/562,302

(22) Filed: Dec. 5, 2014

(65) Prior Publication Data

US 2016/0161483 A1    Jun. 9, 2016

(51) Int. Cl.
*G01N 33/569* (2006.01)
*C12Q 1/68* (2006.01)

(52) U.S. Cl.
CPC ....... *G01N 33/56966* (2013.01); *C12Q 1/6881* (2013.01); *C12Q 2600/158* (2013.01); *G01N 2333/71* (2013.01)

(58) Field of Classification Search
None
See application file for complete search history.

(56) References Cited

FOREIGN PATENT DOCUMENTS

EP    2266628 A2 * 12/2010

OTHER PUBLICATIONS

Seftor et al., Expression of multiple molecular phenotypes by aggressive melanoma tumor cells: role in vasulogenic mimicry, Critical Reviews in Oncology/Hematology 44 (2002) 17-27.*

* cited by examiner

*Primary Examiner* — Suzanne M Noakes
*Assistant Examiner* — Stephen Chong
(74) *Attorney, Agent, or Firm* — Birch, Stewart, Kolasch & Birch, LLP (57) ABSTRACT

A method of distinguishing mesenchymal stem cells (MSCs) in a primary culture of cells derived from a placenta-related tissue is provided. Also provided is a method of increasing the purity of MSC population in a primary culture of cells derived from a placenta-related tissue. Further provided is a method of isolating a MSC population which is more responsive in an inflammatory environment. Said methods each comprise a step of sorting the cells by a marker of EphA2.

18 Claims, 5 Drawing Sheets

METHOD OF DISTINGUISHING MESENCHYMAL STEM CELLS

FIELD OF THE INVENTION

The present invention pertains to a method of distinguishing mesenchymal stem cells (MSCs) in a primary culture of cells derived from a placenta-related tissue. The present invention also relates to a method of increasing the purity of MSC population in a primary culture of cells derived from a placenta-related tissue. In another aspect, the invention pertains to a method of isolating a MSC population which is more responsive in an inflammatory environment.

BACKGROUND OF THE INVENTION

Mesenchymal stem or stromal cells (MSCs) are multipotent cells of embryonic mesodermal origin, with a fibroblast-like morphology. These cells can differentiate into adipocytes, osteocytes, chondrocytes, neural lineage cells, and myocytes among other cell types depending on the stimuli and culture conditions. Although the plasticity of hMSCs and their role in tissue repair and regeneration have been extensively studied, it is their immunological trophic property that has gained the most interest recently [50-51]. Human mesenchymal stem cells have been isolated from a variety of tissues. The most frequently used source of MSCs is the bone marrow (BM). However, the isolation procedure is extremely invasive. To avoid the invasive isolation procedures, tissues such as human umbilical cord and placenta have been considered as good candidates since they are normally discarded after labor. The isolation of hMSCs from umbilical cord or placenta has proven to be efficient by previous studies [49].

MSCs are a subpopulation of a more complex cell composition of stromal cells contained in mesenchymal tissue. Due to the heterogeneous nature and the absence of known biomarkers specific for mesenchymal stem cells, it is a challenging task to define MSC phenotypes and characteristics [52-54]. The molecular components responsible for MSCs functionalities, in particular, those on the plasma membrane, remain largely unknown. In addition, lack of specific cell surface markers renders the cell culture at potential contamination risk with other cell types, in particular, those mature stromal cells such as fibroblasts, which, conversely, are abundant in mesenchymal tissue [52-54]. In the process of isolation of MSCs from placenta-derived tissues, non-MSCs, including fibroblasts, placenta-derived epithelial cells, and placenta-derived reticular cells, often co-exist with MSCs during the in vitro cultivation. In particular, fibroblast is the main source of contamination.

Fibroblasts are considered mature mesenchymal cells that are particularly abundant in the connective tissue. Therefore, these cells are the most frequent contaminating cell phenotype present in many cell culture systems. Not only is it difficult to apply techniques which successfully eliminate fibroblasts from a culture, it is also particularly complex to distinguish MSCs from fibroblasts in the same culture. Fibroblasts and MSCs have an extremely similar morphological appearance; they both proliferate well and share many identical cell surface markers [55, 56]. MSC are currently defined as plastic adherent, multipotent fibroblast-like cells expressing CD73, CD90, CD105 and negative for the hematopoietic markers CD14, CD34 and CD45 by the International Society of Cellular Therapy (ISCT). However, these properties and markers are also shared by fibroblasts. The current definition suggested by ISCT is thus incapable of distinguishing MSC from generic fibroblasts. Until now, the best way to distinguish MSCs from fibroblasts is based on the analysis of the functional properties of these two kinds of cells; MSCs retain multipotent stemness and immunomodulation capacity, while fibroblasts seem more limited in both of these functional properties.

Since Friedenstein's pioneering work in identification of MSCs [48], there are no distinct differences in culture-derivation methodology, morphology, and gene expression signature that consistently and unequivocally distinguish ex vivo culture-expanded MSC from fibroblasts [57-60]. Presently, there is no accepted criterion or single cell-surface marker for separating the MSCs from fibroblasts. Due to the fact that fibroblast is the common contaminant cell population in MSC culture when derived from placenta, a novel surface protein as a biomarker to distinguish MSCs from fibroblasts is crucial to ensure the homogeneity of primary culture of placenta-derived MSCs.

The human erythropoietin-producing hepatocellular (Eph) receptors include transmembrane proteins comprising the largest family of receptor tyrosine kinases (RTKs). The first identified functions of Eph receptors were their roles in the complicated and sophisticated mechanism in axon guidance [4]. Eph receptors are now known to regulate a wide range of cell-to-cell communication events involved in cell positioning and tissue patterning during embryonic development and pathological conditions such as cancer and vascular complications [1-5]. In addition, these receptors are important regulators of specialized cell functions in synaptic plasticity, insulin secretion, bone remodeling, epithelial homeostasis, as well as inflammatory and immune responses [1, 2, 6]. They are expressed by a wide variety of cell types such as neurons, vascular cells, epithelial cells, inflammatory cells, immune cells, and tumor cells including cancer stem cells [7-10].

EphA2 gene belongs to the Eph receptor subfamily of the protein-tyrosine kinase family. Previous studies have been implicated EphA2's functions in mediating developmental events, particularly in the nervous system [4]. During development, EphA2 functions in distinctive aspects of pattern formation and subsequently in development of several fetal tissues, including vasculogenesis, neural tube development, axial mesoderm formation, early hindbrain development, neuron differentiation, regulation of cell migration, bone remodeling through regulation of osteoclastogenesis and osteoblastogenesis, mammary gland epithelial cell proliferation and branching morphogenesis during mammary gland development [11]. In particular, EphA2's role in nervous system embryonic development is well-defined [12], including the process by which neurons send out axons to reach the correct targets.

Roles of Eph receptors have been implicated in stem cell biology only recently, both during embryonic development and in the adult stem cell niche. Eph receptors are expressed in most adult stem cell niches. Stem cells are located in specialized microenvironments, niches, defined as the combination of cellular and microenvironmental determinants orchestrating the self-renewal and differentiation of stem cell pools within specialized tissue locations. The expression of Eph receptors and ephrin ligands during embryogenesis and tissue homeostasis is consistent with their involvement in stem cell regulation during development and in adult tissue homeostasis [13, 15]. It has been suggested Eph/ephrin system carry out a spatio-temporal regulatory function in the balance between stem cell quiescence, self-renewal and differentiation [14]. However, the mechanism of Eph in stem cell niche maintenance and its role in regulating stem cells are not well understood. EphA2 is highly expressed in embryonic stem cells [16]. Nevertheless, the majority of the EphA2 functional studies in stem cells have been focused on the nervous system. EphA2 is highly expressed in CNS, including precursors in neuronal and glial lineages [12, 15]. Recent studies provide evidence that ephrin-A1 promotes the motility of EphA2-positive cardiac stem cells, resulting in enhanced regeneration and cardiac function after myocardial infarction [17]. Beside these findings, the expression profile and functions of EphA2 in stem cell science are not yet well determined.

Eph receptors and ephrin ligands regulate both self-renewal of stem/progenitor cells and tumor progression [14]. High-degree similarity between untransformed stem/progenitor cells and cancer cells is also acknowledged. In recent years the concept of numerous cancers harboring a "cancer stem cell" compartment, comprising up to 25% of the cancer cells population, has been described [14]. These cells have been defined as tumor-propagating cells (TPCs) for their ability to induce tumors in animal hosts, self-renew and give rise to more differentiated cells in expanding tumor cell mass [14]. Recently, Eph/ephrin signals were linked to the regulation of cancer cell dedifferentiation and stem-like properties [9, 18, 19]. However, it is to be noted that cancers stem cells are actually not (multipotent) "stem cells" as generally referred to in the relevant art.

The overexpression of Ephs coupled with the down-regulation of the specific ephrin ligands has been reported in several cancers and associated with tumor aggressiveness and higher grades [19-22]. EphA2 expression is elevated in breast, ovarian, and lung cancer, as well as in glioma and melanoma, and high levels of EphA2 are correlated with poor patient survival [20, 23-29]. However, the roles and the expression of Eph receptor in cancer cells are absolutely context-dependent. A reverse expression pattern has also been observed in some tumors including breast, colorectal cancer, and acute lymphoblastic leukemia, where low Eph receptor expression through epigenetic silencing or mutations correlate with poor prognosis [30]. In the study of transcription profiling by array of human adrenocortical carcinomas, adenomas and healthy adrenal cortex tissues, EphA2 expression was down-regulated in human adrenocortical tumor tissues when compared with healthy adrenal cortex tissues [31]. Hence, although the expression patterns of certain Ephs and ephrins can serve as prognostic markers in many tumorigenesis cases, a reverse phenomenon in substantial amount of study reports was also observed. Expression of Eph/ephrins is critically cell/tumor-context-specific and context-dependent.

Recent studies on glioblastoma (GBM) showed that tumors harboring a large subpopulation of TPCs demonstrate increased expression of EphA2 and EphA3. The EphA2 receptor is overexpressed in human glioblastoma cancer stem cells (CSCs), and EphA2 expression positively correlated with the size and tumor-initiating ability of the CSCs in this specific type of tumor [9]. These Eph receptors regulate central nervous system development whereas their deregulated expression and somatic mutations are associated with growth, progression and metastasis of nervous system tumors [32-36].

On the other hand, ligand-dependent activation of EphA signaling possessing a tumor-suppressive effect in GBM, colorectal, breast, prostate and skin cancer were also reported [27, 38-43]. In substantial GBM studies, activation of EphA2 kinase by ephrinA1 were reported to have an anti-proliferative effect, possibly through down-regulation of EphA2 and FAK activities [27, 38, 44]. EphA2 knockout mice display increased tumor cell proliferation and ERK phosphorylation [45]. Ligand stimulation of EphA2 also attenuates EGF-mediated ERK phosphorylation, which correlates with reduced cell proliferation and migration [46, 47]. Altogether, interestingly, these findings support the tumor growth-suppressive and invasion-suppressive EphA2/ephrinA1 signaling. The result of the ephrin-Eph interaction is remarkably divergent in different contexts.

The research paper published by Vescovi's group in 2012 [9] demonstrating that (1) stem-like tumor-propagating cells (TPCs) in hGBMs highly express EphA2 receptors, (2) high EphA2 expression supports the undifferentiated state and self-renewal in TPCs, (3) TPC content and tumorigenicity are higher in EphA2$^{[High]}$ than EphA2$^{[Low]}$ hGBM cells. Despite the observed facts set forth above, EphA2$^{[Low]}$ hGBM still possess significant tumor-initiating capability. One could argue if EphA2 represents a true TPC marker even in hGBM, let alone in a different tumor or a different type of cells. In other words, one skilled in the art would not have acknowledged that EphA2 is a specific and universal marker for TPCs, much less a specific and universal marker for multipotent stem cells. The same group also filed a patent application claiming the use of EphA2 as a cell surface marker for the identification and the isolation of a stem cell, preferably a mammalian stem cell, more preferably a human or mouse stem cell [37, EP 2733206 A1]. However, in view of that Vescovi's study entirely and only focused on human glioblastomas (hGBMs) and the facts that EphA2$^{[Low]}$ hGBM still possess significant tumor-initiating capability, one skilled in the art would have in no way recognized that EphA2 is a specific marker competent in identifying multipotent stem cells. Further, Vescovi is also silent as to how to distinguishing multipotent stem cells in a primary culture of cells derived from a placenta-related tissue.

BRIEF SUMMARY OF THE INVENTION

It is unexpectedly found in the present invention that mesenchymal stem cells (MSCs) may be distinguished in a primary culture of cells derived from a placenta-related tissue, based on their expression levels of a specific surface marker, EphA2.

Accordingly, in one aspect, the present invention features a method of distinguishing MSCs in a primary culture of cells derived from a placenta-related tissue, comprising sorting the cells by a surface marker of EphA2.

In another aspect, the present invention provides a method of increasing the purity of MSC population in a primary culture of cells derived from a placenta-related tissue, comprising sorting the cells by a surface marker of EphA2.

In a further aspect, the present invention provides a method of isolating a MSC population which is more responsive in an inflammatory environment, comprising sorting the cells by a surface marker of EphA2.

The method of the present invention may be used to distinguish MSCs from a population of cells selected from the group consisting of fibroblasts, placenta-derived epithelial cells, placenta-derived reticular cells, and a combination thereof.

In preferred embodiments of the present invention, the method is used to distinguish MSCs from fibroblasts.

According to the present invention, the placenta-related tissue may be selected from the group consisting of amniotic membrane, chorionic disk, chorionic membrane, and umbilical cord.

According to the present invention, the sorting step may be performed using a technique known or to be developed in the art, for example, an antibody-based or a nucleotide-based isolation method.

In certain embodiments of the present invention, the cells derived from a placenta-related tissue are cultured in a culture medium for MSC.

According to certain embodiments, the isolated MSC population is more responsive to a TNF-α signaling or a TNF-α-dependent signaling.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings:

FIG. 1 shows real-time polymerase chain reaction quantitation of EphA2 transcript. Transcript levels of EphA2 in placenta-derived MSCs were evaluated by fold enrichment compared to the expression of EphA2 in fibroblasts, i.e. by the comparison of the EphA2 mRNA level in MSCs versus the EphA2 level in fibroblasts (MSCs/fibroblasts). Transcript levels of EphA2 in MSCs were demonstrated by the samples from donor #12, #17, #21 and #28. The results showed that EphA2 was highly enriched in MSCs compared with fibroblasts in vitro. D=donor. AM=amniotic membrane; CD=chorionic disk; CM=chorionic membrane; and UC=umbilical cord. BS=fetal bovine serum. P1=passage1. P3=passage3.

FIG. 3 shows the EphA2 RNA levels evaluated by qPCR. The total RNA expression level in different individual cell population was normalized by endogenous GAPDH expression level. "Scramble" represented as scramble control in shRNA knockdown experiment. By comparing to EphA2 transcript expression level in normal wild-type UC-derived MSC, the qRT-PCR results confirmed the sh-EphA2 knockdown efficiency. D=donor. UC=umbilical cord.

In FIG. 4A, viable migrated cells are presented as CellTiter-Glo® Luminescent signal intensity. In FIG. 4B, viable migrated cells are presented as relative proportion compared to wild-type MSC in 0.2% FBS control.

DETAILED DESCRIPTION OF THE INVENTION

The present invention is based on the unexpected finding that through a cell sorting by surface marker EphA2, mesenchymal stem cells (MSCs) can be distinguished in a primary culture of cells derived from a placenta-related tissue.

In one aspect, the present invention provides a method of distinguishing MSCs in a primary culture of cells derived from a placenta-related tissue, comprising sorting the cells by a surface marker of EphA2.

In another aspect, the invention features a method of increasing the purity of MSC population in a primary culture of cells derived from a placenta-related tissue, comprising sorting the cells by a surface marker of EphA2.

It is also demonstrated that the EphA2-sorted MSCs exhibit superior responsiveness in an inflammatory environment as compared with unsorted MSCs or MSC like cells. Accordingly, in a further aspect, the invention provides a method of isolating a MSC population which is more responsive in an inflammatory environment or microenvironment, comprising sorting the cells by a surface marker of EphA2. In one embodiment of the present invention, the isolated MSC population is more responsive to a TNF-α signaling or a TNF-α-dependent signaling.

MSCs demonstrate immunosuppressive functionality by suppressing T- and B-cell responses following activation by various cytokines. They also can be induced to exert pro-inflammatory effects in the presence of acute inflammatory environment due to the actions of TNF-α and IFN-γ. In inflammatory joint diseases such as rheumatoid arthritis, MSCs in bone marrow migrate to joints by a TNF-α-dependent mechanism and may be in part responsible for the disease process. MSCs have also been demonstrated in increased numbers in periarticular tissues in osteoarthritis, which may reflect an attempt at joint repair or regeneration [6]. It has been proposed that TNF-α released in inflammatory environment confers immunosuppressive properties upon MSCs by binding to MSCs' TNF-R1 and activating the NF-κB pathway in MSCs, resulting in MSCs to exercise the role in immunomodulation [62].

According to the present invention, the cells are freshly derived, obtained or collected from a placenta-related tissue following a protocol known in the art, for example, that of Fukuchi et al. In certain preferred embodiments, the cells derived from a placenta-related tissue are then cultured in a culture medium for MSC. A standard medium for MSC comprises Minimum Essential Medium Eagle (with different versions of modification), fetal bovine serum (FBS), and basic fibroblast growth factor (bFGF) [49, 64-68].

According to the present invention, the method may be used to distinguish MSCs from a population of cells selected from the group consisting of fibroblasts, placenta-derived epithelial cells, placenta-derived reticular cells, and a combination thereof. Preferably, methods of the present invention are used to distinguish MSCs from fibroblasts in a primary culture of cells derived from a placenta-related tissue.

The placenta-related tissue may be selected from the group consisting of amniotic membrane, chorionic disk, chorionic membrane, and umbilical cord.

In carrying out the methods of the present invention, a culture of a primary culture of cells derived from a placenta-related tissue is subjected to a cell sorting by EphA2. The cell sorting may be performed through a technique known or to be developed in the art, for example, an antibody-based or a nucleotide-based isolation method. Preferably, the cell sorting is performed by an antibody-based magnetic cell sorting. For example, the MACS method (MACS® Technology, Miltenyi Biotec). In addition, the cell sorting may be preform through a flow cytometry method, e.g. an antibody-based or a nucleotide-based flow cytometry.

As used herein, the term "more responsive" refers to MSCs' cellular behaviors (e.g. mobility) responding to an inflammatory related signaling pathway, including but not limited to a TNF-α signaling or a TNF-α-dependent signaling.

The present invention is further illustrated by the following examples, which are provided for the purpose of demonstration rather than limitation.

EXAMPLES

Example 1

The Immunophenotypic Characterization of the Placenta-Derived Mesenchymal Stem Cells (MSCs) and Fibroblasts Full-term placentas (n=8) were collected after obtaining written informed consent from donors. MSCs were derived from amniotic membrane (AM), chorionic disk (CD), chorionic membrane (CM), and umbilical cord (UC). Placenta-derived cells were cultured, expanded and maintained in α-MEM with FBS and basic FGF at 37° C., saturating humidity and 5% $CO_2$, and were sub-cultured when cells reached 80% confluence, later phenotypically characterized by flow cytometry. In the process of immunostaining subject to flow cytometry, cells were incubated with the antibodies following manufacturer's instructions. Nonspecific IgG of the corresponding class served as the negative control. Cell suspensions were analyzed on a flow cytometer (BD Biosciences FACSCanto II) with Flowjo 7.6.1 software.

We assessed expression of CD11b, CD19, CD34, CD45, CD73, CD90, CD105, HLA-DR, and EphA2. Flow cytometry analysis of all MSCs isolated from the various locations of a placenta were positive for the CD73, CD90, CD105, EphA2, and negative for CD11b, CD19, CD34, CD45, HLA-DR. Flow cytometry analysis of fibroblasts (Human Foreskin Fibroblasts, neonatal, PC501A-HFF, SBI) was positive for the CD73, CD90, CD105, negative for CD11b, CD19, CD34, CD45, HLA-DR, and negative or low for EphA2. A distinct pattern was noted for EphA2 between placenta-derived MSCs and fibroblasts: MSCs showed high percentage of EphA2-positive cells, whereas fibroblasts showed the inverse. The results are shown in Table 1 below.

TABLE 1

Immunophenotypes of placenta-derived mesenchymal stem cells and fibroblasts (percentage of positive cells on flow cytometry)

| Donor/Tissue | Cell Surface Marker | | | | |
| --- | --- | --- | --- | --- | --- |
| | CD73 | CD90 | CD105 | EphA2 | Negative Cocktail |
| D12AM | 99.6 | 99.6 | 75.9 | 80.0 | 0.6 |
| D12CD | 99.3 | 99.5 | 97.0 | 72.9 | 0.5 |
| D12CM | 99.3 | 98.0 | 98.0 | 77.7 | 2.3 |
| D12UC | 99.4 | 99.7 | 90.6 | 80.2 | 0.7 |
| D17AM | 99.7 | 95.7 | 89.4 | 62.7 | 0.6 |
| D17CD | 99.7 | 95.7 | 92.1 | 45.0 | 0.6 |
| D17CM | 99.6 | 77.8 | 88.2 | 80.7 | 1.0 |
| D17UC | 99.6 | 99.8 | 84.9 | 65.9 | 1.4 |
| Fibroblasts | 99.3 | 97.7 | 75.6 | 18.6 | 0.6 |

AM = amniotic membrane; CD = chorionic disk; CM = chorionic membrane; and UC = umbilical cord.
Negative Cocktail includes the antibodies against CD11b, CD19, CD34, CD45, and HLA-DR (Human MSC Analysis Kit, BD Stemflow™, catalog number 562245).

The Immunophenotypes of placenta-derived mesenchymal stem cells were demonstrated by samples from donor #12 and donor #17 at P0. Flow cytometry analysis revealed that the populations of MSCs were 99.3~99.7% CD73 positive, 77.8~99.8% CD90 positive, 75.9~98.0% CD 105 positive, and 45.0~80.7% EphA2 at P0. In contrast, hematopoietic cell lineage-specific markers, such as CD11b, CD19, CD34, CD45 and HLA-DR, were not expressed in MSCs. Flow cytometry analysis of fibroblasts revealed that the population were 99.3% CD73 positive, 97.7% CD90 positive, 75.6% CD 105 positive, and 18.6% EphA2 positive; hematopoietic cell lineage-specific markers, such as CD11b, CD19, CD34, CD45 and HLA-DR, were not expressed in fibroblasts.

Example 2

The Immunophenotypic Characterization of the EphA2-Sorted Placenta-Derived Mesenchymal Stem Cells (MSCs)

a. Flow Cytometry Analysis of EphA2-Enriched MSCs Sorted by Magnetic-Activated Cell Sorting (MACS)

The MACS method (MACS® Technology, Miltenyi Biotec) allows cells to be separated by incubating with magnetic nanoparticles coated with antibodies against EphA2 surface antigen. Primary culture of MSCs derived from placenta were incubated with the fluorescence conjugated anti-human antibodies against EphA2 and sorted by R-Phycoerythrin (PE) Magnetic Particles according to manufacturer's instructions. Flow cytometry analysis of MACS sorted MSCs at P0 revealed that cell population could become homogeneous in 100% CD73 positive, 97.2~99.5% CD90 positive, 96.0~99.9% CD 105 positive and 96.6~100% EphA2 positive expression since passage 0 (see Table 2 below), demonstrating that EphA2 sorting via antibodies conjugated magnetic beads could dramatically improve the MSC purity from P0. The enriched EphA2-positive MSCs population could be well maintained in in vitro expansion to later passage (see Table 3 below).

TABLE 2

The immunophenotypic characterization of the EphA2-sorted placenta-derived MSCs at P0 (percentage of positive cells on flow cytometry)

| Cell population | Cell surface markers | | | |
| --- | --- | --- | --- | --- |
| | CD 73 | CD 90 | CD 105 | EphA2 |
| D17CDP0_unsorted | 99.7 | 95.7 | 92.1 | 45.0 |
| D17CDP0_EphA2-sorted | 100.0 | 97.2 | 98.0 | 96.6 |

The immunophenotypic characterization of the EphA2-sorted MSCs was demonstrated by the MSCs derived from chorionic disk (CD) from donor #17 at P0. The results showed that EphA2-positive cells were also CD73 positive, CD90 positive and CD105 positive. D=donor. P=passage.

TABLE 3

The immunophenotypic characterization of the EphA2-MACS-enriched population during the in vitro expansion (percentage of positive cells on flow cytometry)

| Cell population | Cell surface markers | | | |
| --- | --- | --- | --- | --- |
| | CD 73 | CD 90 | CD 105 | EphA2 |
| D17CDP0_EphA2-sorted | 100.0 | 97.2 | 98.0 | 96.6 |
| D17CD_EphA2+_P1 | 100.0 | 99.5 | 99.9 | 100.0 |
| D17CD_EphA2+_P2 | 100.0 | 99.3 | 99.9 | 99.9 |
| D17CD_EphA2+_P3 | 100.0 | 99.5 | 99.9 | 100.0 |

The immunophenotypic characterization of the EphA2-sorted MSCs in later expansion. Immunophenotype was demonstrated by the MSCs derived from chorionic disk (CD) from donor #17. MSCs were sorted by EphA2-antibodies-conjugated magnetic beads at P0, and maintained in optimized MSCs cultural condition in later passages during in vitro expansion. The results showed that expression of cell surface marker EphA2 could be well maintained in later passages in optimized MSCs cultivation conditions.

b. Flow Cytometry Analysis of EphA2-Enriched MSCs Sorted by Flow Cytometry Cell Sorter (FCCS)

Cells derived from placenta were harvested and sorted by anti-EphA2 antibodies via JAZZ cell sorter (BD, USA) at P0. Flow cytometry analysis of EphA2-sorted MSCs revealed that there were 99.5~100% CD73 & CD90 double positive, 99.6~100% CD105 & CD90 double positive, 99.5~100% EphA2 & CD90 double positive, 99.8~100% CD73 & EphA2 double positive, 99.5~100% CD105 & EphA2 double positive and 99.7~100% CD73 & CD105 double positive populations in passage 2~6 (see Table 4 below). The data revealed that EphA2 protein could be continuously expressed and maintained in MSCs culture at later passages.

TABLE 4

The immunophenotypic characterization of the EphA2-FCCS-enriched population during the in vitro expansion

| % | $CD73^+$ $CD90^+$ | $CD105^+$ $CD90^+$ | $EphA2^+$ $CD90^+$ | $CD73^+$ $EphA2^+$ | $CD105^+$ $EphA2^+$ | $CD73^+$ $CD105^+$ |
|---|---|---|---|---|---|---|
| P2 | 100 | 100 | 99.5 | 100 | 99.8 | 99.7 |
| P3 | 99.5 | 99.6 | 99.5 | 99.8 | 99.5 | 99.7 |
| P4 | 99.9 | 99.7 | 99.9 | 100 | 99.6 | 99.7 |
| P6 | 100 | 99.9 | 100 | 99.9 | 100 | 100 |

The immunophenotypic characterization of the EphA2-enriched MSCs in later expansion. Immunophenotype was demonstrated by the MSCs derived from the umbilical cord (UC) from donor #7. MSCs were sorted by anti-EphA2 antibodies via cell sorter at P0, and maintained in optimized MSCs cultural condition in later passages during in vitro expansion. The expression of cell surface marker EphA2 could be well preserved in later passages.

Example 3

Quantitative Real-Time PCR Evaluation of EphA2 Transcript in Placenta-Derived Mesenchymal Stem Cells (MSCs) and Fibroblasts Total RNA from 64 populations of placenta-derived cells (n=8, including passage 1 and passage 3, from AM, CD, CM, UC, 4 different parts of a placenta) and Human Foreskin Fibroblasts (neonatal, PC501A-HFF, SBI) were isolated using the Direct-zol miniprep Kit (Zymo Research Corporation, CA, USA). The complementary DNA (cDNA) was synthesized with Transcriptor First Strand cDNA Synthesis Kit (Roche, Basel, Switzerland). Then Quantitative RT-PCR was performed using the Roche Universal ProbeLibrary System with a LightCycler480 II (Roche, Basel, Switzerland) according to the manufacturer's instructions.

Figure 1:
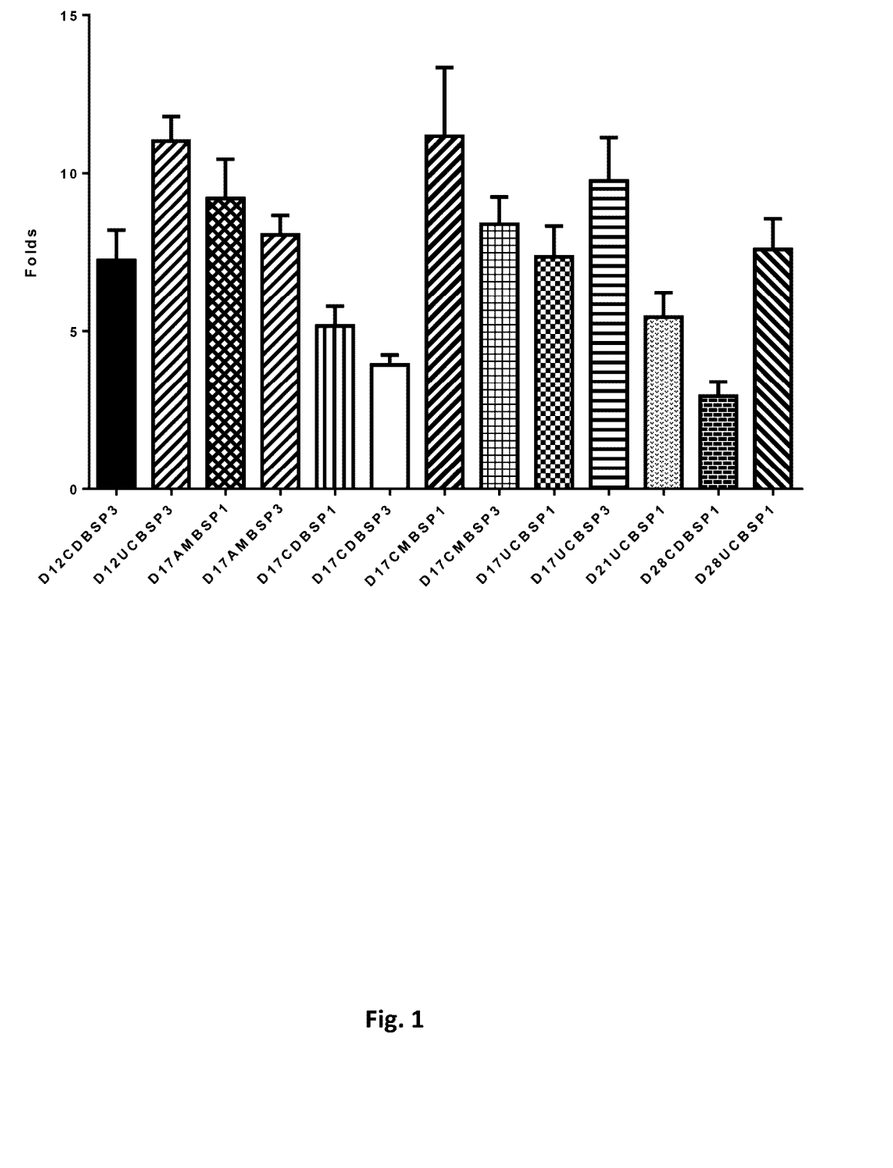

We assessed expression of EphA2 by quantitative real-time PCR in order to compare placenta-derived multipotent MSCs and fibroblasts. Gene expression was normalized to the endogenous gene glyceraldehyde-3-phosphate dehydrogenase expression in the different cell populations. The expression of EphA2 transcript in MSCs was calculated by fold enrichment compared to the expression of EphA2 in fibroblasts. The results showed that EphA2 was highly expressed in MSCs when compared with fibroblasts (FIG. 1).

Example 4

Flow Cytometry Analysis of Mixed Populations of MSCs and Fibroblast

Figure 2:
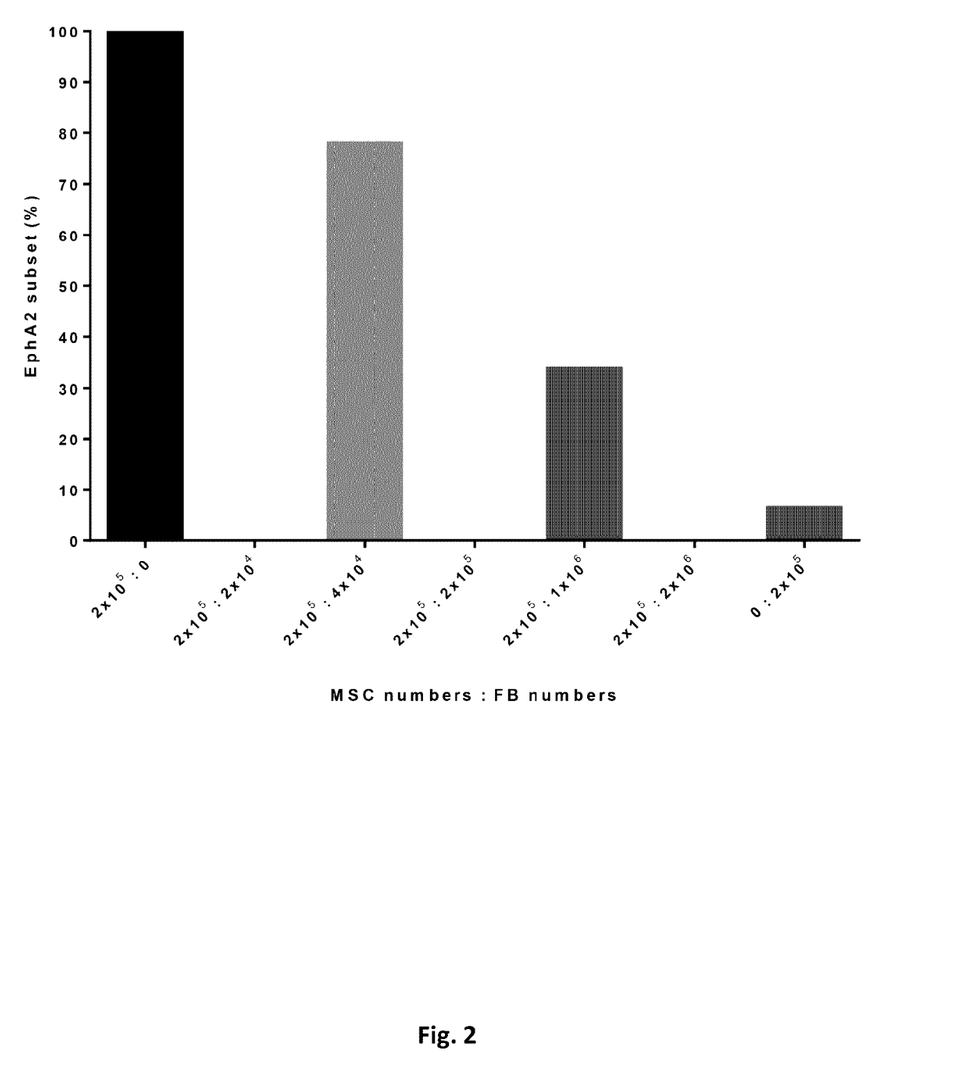
FIG. 2 shows the results of Flow Cytometry analysis of mixed populations of MSCs and fibroblasts. MSCs derived from the umbilical cord (UC) from donor #23 were mixed with fibroblasts in different ratios. The results demonstrated that the percentage of EphA2$^+$ population detected by flow cytometry decreased proportionally in response to the increased fibroblast population. FB=fibroblasts.

To demonstrated that EphA2 could serve as a biomarker to separate placenta-derived MSC from fibroblasts, MSCs derived from the umbilical cord (UC) from donor #23 were mixed with fibroblasts in Eppendorf tubes by following ratios (MSC: fibroblasts in cell number): $2 \times 10^5$: 0, $2 \times 10^5$: $2 \times 10^4$, $2 \times 10^5$: $4 \times 10^4$, $2 \times 10^5$: $2 \times 10^5$, $2 \times 10^5$: $1 \times 10^6$, $2 \times 10^5$: $2 \times 10^6$ and 0: $2 \times 10^5$. $EphA2^+$ population in each Eppendorf tube was then analyzed by flow cytometry. The results shown in FIG. 2 demonstrated that the percentage of $EphA2^+$ population detected by anti-EphA2 antibodies via flow cytometry decreased proportionally in response to the increased fibroblasts population.

Example 5

EphA2 Knockdown by Lentiviral Transduction

Figure 3:
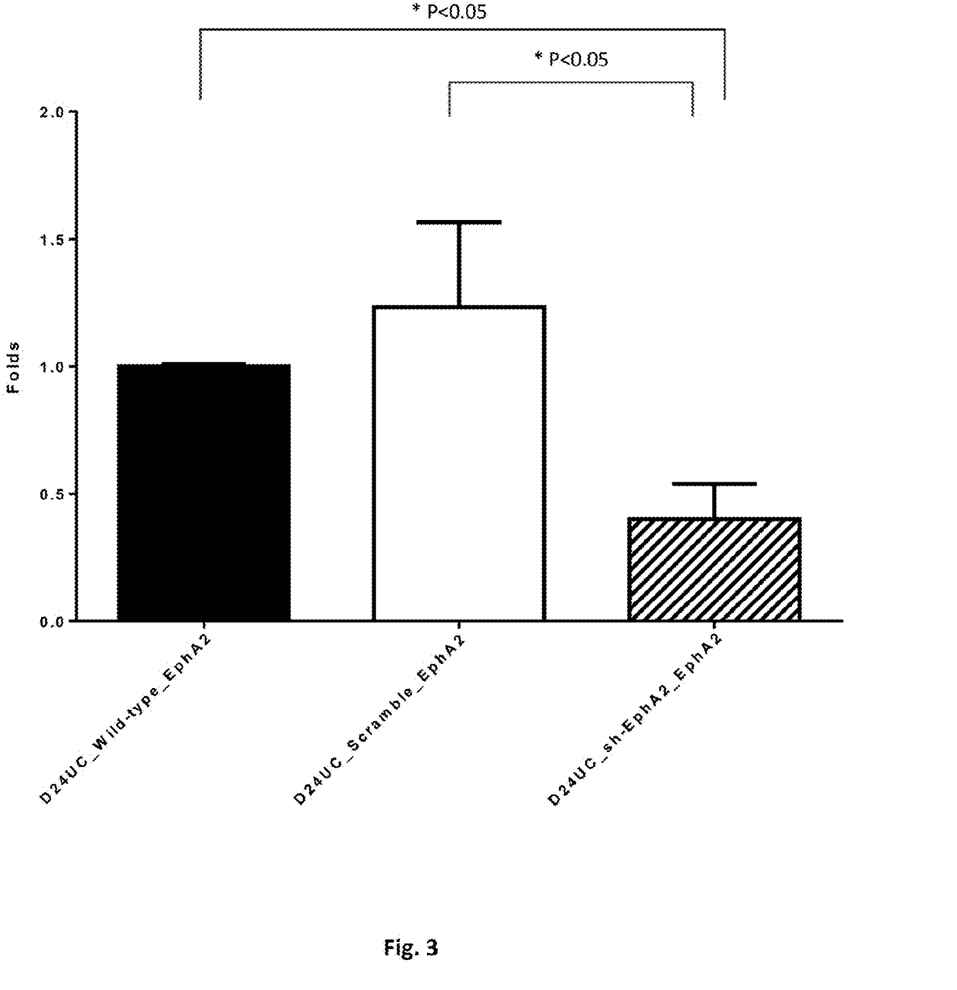

In order to evaluate the functions of EphA2 in the isolated MSCs population, shRNA (shEphA2) knockdown experiment by lentiviral transduction was carried out. Each construct has an EGFP reporter to monitor transduction efficiency. Four different shRNA sequences were tested, each with three different Multiplicity Of Infection (MOI) (2, 5, 10), and each experimental condition was performed in triplicate. Knockdown efficiency was evaluated by qRT-PCR. The results are shown in FIG. 3. A best knockdown efficiency of 50% knockdown could be achieved.

Example 6

In this study, we investigated the role of EphA2 in MSCs in response to inflammatory stimuli, such as TNF-α signal, in vitro. We focused on the effect of EphA2 involved in MSCs migration during inflammation [51, 63]. The mobility of $EphA2^{high}$ MSCs and $EphA2^{low}$ MSCs under basal culture conditions or in the presence of TNF-α inflammatory stimuli was examined.

a. Trans-Well Migration Analysis of EphA2-Knockdown MSCs

Figure 4A:
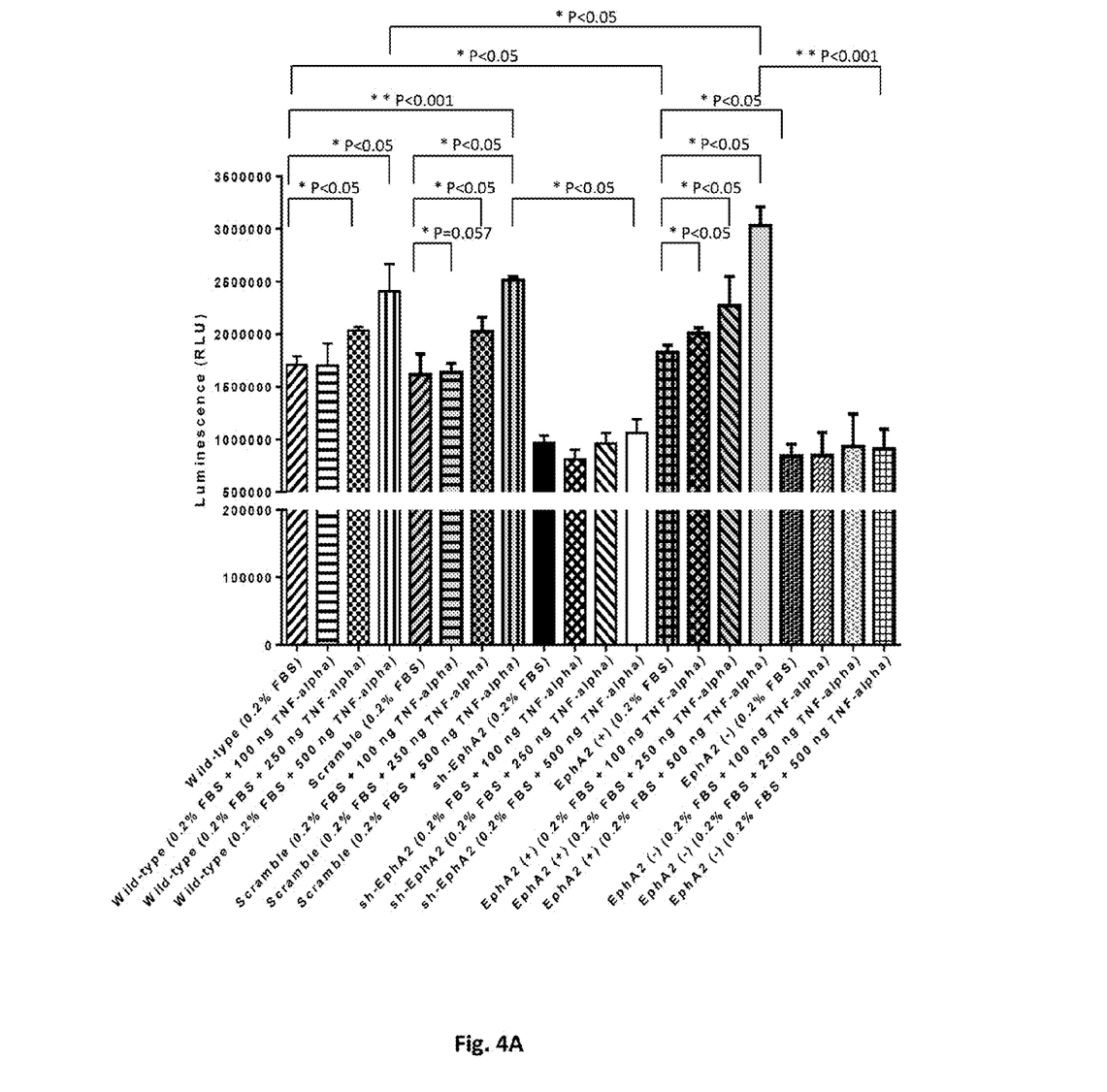
FIG. 4A and FIG. 4B show the results of trans-well migration assay and cell viability detection.
Figure 4B:
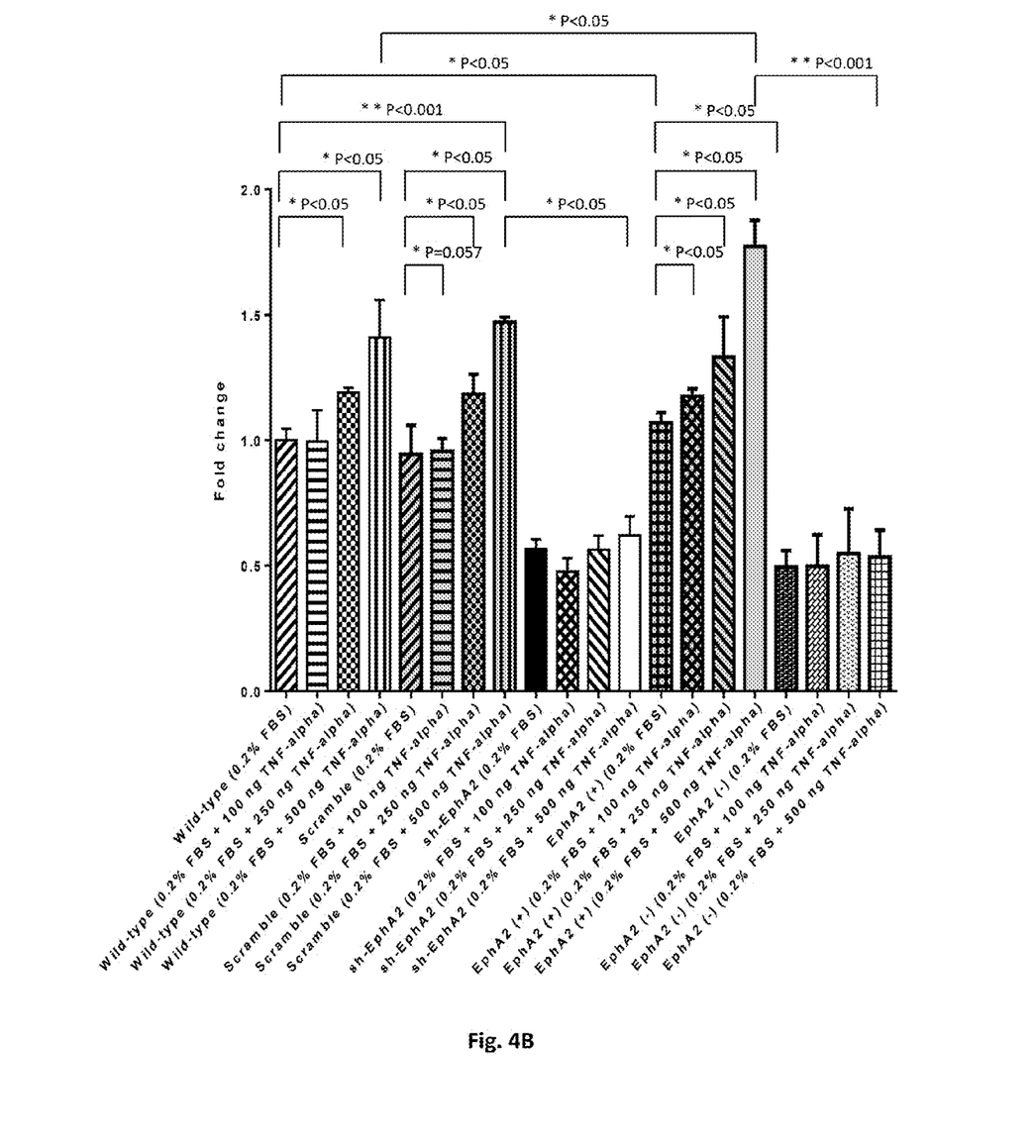

The wild-type, sh-scramble and sh-EphA2 targeted MSCs were cultured with a condition of 30,000 cells in 8 μm trans-wells. 0.2% FBS and TNF-α were added in lower chamber to activate the MSCs migration. After 6 hours, viable migrated cells were detected via CellTiter-Glo® Luminescent reagents according to manufacturer's instructions. The results are shown in FIGS. 4A and 4B. The data revealed that capability to respond to TNF-α signal and migration of sh-EphA2 MSCs was compromised by EphA2 knock down.

b. Trans-Well Migration Analysis of EphA2high MSCs

Primary culture of cells derived from placenta were incubated with the magnetic beads conjugated by anti-human antibodies against EphA2, and were then sorted by positive selection according to manufacturer's instructions. Flow cytometry analysis confirmed the $EphA2^+$ MSCs and $EphA2^-$ cell populations after MACS sorting. Cells were cultured with a condition of 30,000 cells in 8 μm trans-wells. 0.2% FBS and TNF-α were added in lower chamber to activate the MSCs migration. After 6 hours, viable migrated cells were detected via CellTiter-Glo® Luminescent reagents according to manufacturer's manual. The data revealed that capability to respond to TNF-α signal and migration of MSCs was enhanced in EphA2-enriched population.

As shown in FIGS. 4A and 4B, the migration of MSCs was significantly affected by the addition of TNF-α to the basal medium. After stimulation of MSCs with TNF-α, migration of MSCs, detected via CellTiter-Glo® Luminescent reagents, was increased in TNF-α-dose-dependant manner (see FIG. 4A). In contrast, mobility of cells was abolished in EphA2-knockdown MSCs population, or in EphA2⁻ cells by sorting. The effect of EphA2 molecule in the migration of MSCs in response to TNF-α signal is more obvious when the luminescent signal was converted to migrated cell population relative to migrated wild-type MSCs in 0.2% FBS control in fold change (see FIG. 4B).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

REFERENCES

[1] Pasquale E B (2008) Eph-ephrin bidirectional signaling in physiology and disease. Cell 133:38-52.

[2] Pasquale E B (2010) Eph receptors and ephrins in cancer: bidirectional signalling and beyond. Nat Rev Cancer 10:165-180.

[3] Nievergall E, Lackmann M, Janes P W (2012) Eph-dependent cell-cell adhesion and segregation in development and cancer. Cell Mol Life Sci 69:1813-1842.

[4] Wilkinson D G (2001) Multiple roles of EPH receptors and ephrins in neural development. Nat Rev Neurosci 2:155-164.

[5] Pitulescu M E, Adams R H (2010) Eph/ephrin molecules—a hub for signaling and endocytosis. Genes Dev 24:2480-2492.

[6] Miao H, Wang B (2009) Eph/ephrin signaling in epithelial development and homeostasis. Int J Biochem Cell Biol 41:762-770.

[7] Palmer A, Klein R (2003) Multiple roles of ephrins in morphogenesis, neuronal networking, and brain function. Genes Dev 17:1429-1450.

[8] Hafner C, Schmitz G, Meyer S, Bataille F, Hau P, Langmann T, Dietmaier W, Landthaler M, Vogt T (2004) Differential gene expression of Eph receptors and ephrins in benign human tissues and cancers. Clin Chem 50:490-499.

[9] Binda E, Visioli A, Giani F, Lamorte G, Copetti M, Pitter K L, Huse J T, Cajola L, Zanetti N, DiMeco F, De Filippis L, Mangiola A, Maira G, Anile C, De Bonis P, Reynolds B A, Pasquale E B, Vescovi A L (2012) The EphA2 receptor drives self-renewal and tumorigenicity in stem-like tumor-propagating cells from human glioblastomas. Cancer Cell 22:765-780.

[10] Day B W, Stringer B W, Al-Ejeh F, Ting M J, Wilson J, Ensbey K S, Jamieson P R, Bruce Z C, Lim Y C, Offenhauser C, Charmsaz S, Cooper L T, Ellacott J K, Harding A, Leveque L, Inglis P, Allan S, Walker D G, Lackmann M, Osborne G, Khanna K K, Reynolds B A, Lickliter J D, Boyd A W (2013) EphA3 maintains tumorigenicity and is a therapeutic target in glioblastoma multiforme. Cancer Cell 23:238-248.

[11] Huntley R P, Sawford T, Mutowo-Muellenet P, Shypitsyna A, Bonilla C, Martin M J, O'Donovan C. (2014) The GOA database: Gene Ontology annotation updates for 2015. Nucleic Acids Research 2014 doi: 10.1093/nar/gku1113.

[12] Purves D, Augustine G J, Fitzpatrick D, et al., editors. Neuroscience. 2001.

[13] Conover J C, Doetsch F, Garcia-Verdugo J M, Gale N W, Yancopoulos G D, Alvarez-Buylla A (2000) Disruption of Eph/ephrin signaling affects migration and proliferation in the adult subventricular zone. Nat Neurosci 3:1091-1097.

[14] Erika Gucciardo, Nami Sugiyama and Kaisa Lehti (2014) Eph- and ephrin-dependent mechanisms in tumor and stem cell dynamics. Cell Mol Life Sci. 2014 October; 71(19):3685-710.

[15] M. Aoki, T. Yamashita, M. Tohyama EphA receptors direct the differentiation of mammalian neural precursor cells through a mitogen-activated protein kinase-dependent pathway. J Biol Chem, 279 (2004), pp. 32643-32650.

[16] Lickliter J D, Smith F M, Olsson J E, Mackwell K L, Boyd A W (1996) Embryonic stem cells express multiple Eph-subfamily receptor tyrosine kinases. Proc Natl Acad Sci USA 93:145-150.

[17] P. Goichberg, Y. Bai, D. D'Amario, J. Ferreira-Martins, C. Fiorini, H. Zheng, et al. The ephrin A1-EphA2 system promotes cardiac stem cell migration after infarction. Circ Res, 108 (2011), pp. 1071-1083.

[18] Day B W, Stringer B W, Al-Ejeh F, Ting M J, Wilson J, Ensbey K S, Jamieson P R, Bruce Z C, Lim Y C, Offenhauser C, Charmsaz S, Cooper L T, Ellacott J K, Harding A, Leveque L, Inglis P, Allan S, Walker D G, Lackmann M, Osborne G, Khanna K K, Reynolds B A, Lickliter J D, Boyd A W (2013) EphA3 maintains tumorigenicity and is a therapeutic target in glioblastoma multiforme. Cancer Cell 23:238-248.

[19] H. Miao, N. W. Gale, H. Guo, J. Qian, A. Petty, J. Kaspar, et al. EphA2 promotes infiltrative invasion of glioma stem cells in vivo through cross-talk with Akt and regulates stem cell properties (2014) Oncogene.

[20] Brantley-Sieders D M, Jiang A, Sarma K, Badu-Nkansah A, Walter D L, Shyr Y, Chen J (2011) Eph/ephrin profiling in human breast cancer reveals significant associations between expression level and clinical outcome. PLoS ONE 6:e24426.

[21] Castano J, Davalos V, Schwartz S Jr, Arango D (2008) EPH receptors in cancer. Histol Histopathol 23:1011-1023.

[22] Wang X D, Reeves K, Luo F R, Xu L A, Lee F, Clark E, Huang F (2007) Identification of candidate predictive and surrogate molecular markers for dasatinib in prostate cancer: rationale for patient selection and efficacy monitoring. Genome Biol 8:R255.

[23] J. M. Brannan, W. Dong, L. Prudkin, C. Behrens, R. Lotan, B. N. Bekele, et al. (2009) Expression of the receptor tyrosine kinase EphA2 is increased in smokers and predicts poor survival in non-small cell lung cancer. Clin Cancer Res, 15 (2009), pp. 4423-4430.

[24] L. Faoro, P. A. Singleton, G. M. Cervantes, F. E. Lennon, N. W. Choong, R. Kanteti, et al. (2010) EphA2 mutation in lung squamous cell carcinoma promotes increased cell survival, cell invasion, focal adhesions, and mTOR activation J Biol Chem, 285 (2010), pp. 18575-18585.

[25] M. S. Kinch, M. B. Moore, D. H. J. Harpole (2003) Predictive value of the EphA2 receptor tyrosine kinase in lung cancer recurrence and survival. Clin Cancer Res, 9 (2003), pp. 613-618.

[26] F. Liu, P. J. Park, W. Lai, E. Maher, A. Chakravarti, L. Durso, et al. (2006) A genome-wide screen reveals functional gene clusters in the cancer genome and identifies EphA2 as a mitogen in glioblastoma. Cancer Res, 66 (2006), pp. 10815-10823.

[27] J. Wykosky, D. M. Gibo, C. Stanton, W. Debinski (2005) EphA2 as a novel molecular marker and target in glioblastoma multiforme. Mol Cancer Res, 3 (2005), pp. 541-551.

[28] C. N. Landen, M. S. Kinch, A. K. Sood (2005) EphA2 as a target for ovarian cancer therapy. Expert Opin Ther Targets, 9 (2005), pp. 1179-1187.

[29] D. Udayakumar, G. Zhang, Z. Ji, C. N. Njauw, P. Mroz, H. Tsao (2011) EphA2 is a critical oncogene in melanoma. Oncogene, 30 (2011), pp. 4921-4929.

[30] Kuang S Q, Bai H, Fang Z H, Lopez G, Yang H, Tong W, Wang Z Z, Garcia-Manero G (2010) Aberrant DNA methylation and epigenetic inactivation of Eph receptor tyrosine kinases and ephrin ligands in acute lymphoblastic leukemia. Blood 115:2412-2419.

[31] Giordano T J, Kuick R, Else T, Gauger P G, Vinco M, Bauersfeld J, Sanders D, Thomas D G, Doherty G, Hammer G. (2009) Molecular classification and prognostication of adrenocortical tumors by transcriptome profiling. Clin Cancer Res. 2009 Jan. 15; 15(2):668-76.

[32] Wykosky J, Gibo D M, Stanton C, Debinski W (2005) EphA2 as a novel molecular marker and target in glioblastoma multiforme. Mol Cancer Res 3:541-551.

[33] Cheng H J, Nakamoto M, Bergemann A D, Flanagan J G (1995) Complementary gradients in expression and binding of ELF-1 and Mek4 in development of the topographic retinotectal projection map. Cell 82:371-381.

[34] Sefton M, Araujo M, Nieto M A (1997) Novel expression gradients of Eph-like receptor tyrosine kinases in the developing chick retina. Dev Biol 188:363-368.

[35] Brittis P A, Lu Q, Flanagan J G (2002) Axonal protein synthesis provides a mechanism for localized regulation at an intermediate target. Cell 110:223-235.

[36] Tanaka M, Ohashi R, Nakamura R, Shinmura K, Kamo T, Sakai R, Sugimura H (2004) Tiam1 mediates neurite outgrowth induced by ephrin-B1 and EphA2. EMBO J 23:1075-1088.

[37] Method for the isolation for mammalian stem cells using EphA2 and uses thereof. EP 2733206 A1.

[38] Wykosky J, Palma E, Gibo D M, Ringler S, Turner C P, Debinski W (2008) Soluble monomeric EphrinA1 is released from tumor cells and is a functional ligand for the EphA2 receptor. Oncogene 27:7260-7273.

[39] Miao H, Li D Q, Mukherjee A, Guo H, Petty A, Cutter J, Basilion J P, Sedor J, Wu J, Danielpour D, Sloan A E, Cohen M L, Wang B (2009) EphA2 mediates ligand-dependent inhibition and ligand-independent promotion of cell migration and invasion via a reciprocal regulatory loop with Akt. Cancer Cell 16:9-20.

[40] Noblitt L W, Bangari D S, Shukla S, Knapp D W, Mohammed S, Kinch M S, Mittal S K (2004) Decreased tumorigenic potential of EphA2-overexpressing breast cancer cells following treatment with adenoviral vectors that express EphrinA1. Cancer Gene Ther 11:757-766.

[41] Chiu S T, Chang K J, Ting C H, Shen H C, Li H, Hsieh F J (2009) Over-expression of EphB3 enhances cell-cell contacts and suppresses tumor growth in HT-29 human colon cancer cells. Carcinogenesis 30:1475-1486.

[42] Noren N K, Foos G, Hauser C A, Pasquale E B (2006) The EphB4 receptor suppresses breast cancer cell tumorigenicity through an Abl-Crk pathway. Nat Cell Biol 8:815-825.

[43] Teng L, Nakada M, Furuyama N, Sabit H, Furuta T, Hayashi Y, Takino T, Dong Y, Sato H, Sai Y, Miyamoto K, Berens M E, Zhao S G, Hamada J (2013) Ligand-dependent EphB1 signaling suppresses glioma invasion and correlates with patient survival. Neuro Oncol 15:1710-1720.

[44] Liu D P, Wang Y, Koeffler H P, Xie D (2007) Ephrin-A1 is a negative regulator in glioma through down-regulation of EphA2 and FAK. Int J Oncol 30:865-871.

[45] Guo H, Miao H, Gerber L, Singh J, Denning M F, Gilliam A C, Wang B (2006) Disruption of EphA2 receptor tyrosine kinase leads to increased susceptibility to carcinogenesis in mouse skin. Cancer Res 66:7050-7058.

[46] Macrae M, Neve R M, Rodriguez-Viciana P, Haqq C, Yeh J, Chen C, Gray J W, McCormick F (2005) A conditional feedback loop regulates Ras activity through EphA2. Cancer Cell 8:111-118.

[47] Zou J X, Wang B, Kalo M S, Zisch A H, Pasquale E B, Ruoslahti E (1999) An Eph receptor regulates integrin activity through R-Ras. Proc Natl Acad Sci USA 96:13813-13818.

[48] Friedenstein A J, Petrakova K V, Kurolesova A I, Frolova G P (1968) Heterotopic of bone marrow. Analysis of precursor cells for osteogenic and hematopoietic tissues. Transplantation 6:230-47.

[49] Fukuchi Y, Nakajima H, Sugiyama D, Hirose I, Kitamura T, Tsuji K. Human placenta-derived cells have mesenchymal stem/progenitor cell potential. Stem Cells. 2004; 22(5):649-58.

[50] Stagg J, Galipeau J. (2013) Mechanisms of immune modulation by mesenchymal stromal cells and clinical translation. Curr Mol Med. 13(5):856-67.

[51] Casado J G, Tarazona R, Sanchez-Margallo F M. (2013) N K and MSCs crosstalk: the sense of immunomodulation and their sensitivity. Stem Cell Rev. 9(2):184-9.

[52] Javazon E H, Beggs K J, Flake A W. (2004) Mesenchymal stem cells: paradoxes of passaging. *Exp Hematol.* 32(5):414-25.

[53] Nombela-Arrieta C, Ritz J, Silberstein L E. (2011) The elusive nature and function of mesenchymal stem cells. Nat Rev Mol Cell Biol. 12(2):126-31.

[54] Keating A. (2012) Mesenchymal stromal cells: new directions. *Cell Stem Cell.* 10(6):709-16.

[55] Linge C, Green M R, Brooks R F. A method for removal of fibroblasts from human tissue culture system. Exp Cell Res 1989, 185:519-528.

[56] Lorenz K, Sicker M, Schmelzer E, Rupf T, Salvetter J, Schulz-Siegmund M, Bader A: Multilineage differentiation potential of human dermal skin-derived fibroblasts. Exp Dermatol 2008, 17:925-932.

[57] Blasi et al., (2011) Dermal fibroblasts display similar phenotypic and differentiation capacity to fat-derived mesenchymal stem cells, but differ in anti-inflammatory and angiogenic potential. Vascular Cell 2011, 3:5.

[58] Covasa et al., (2008) Multipotent mesenchymal stromal cells obtained from diverse human tissues share functional properties and gene-expression profile with CD146+ perivascular cells and fibroblasts. Experimental Hematology. Volume 36, Issue 5, Pages 642-654.

[59] Muzlifah A. Haniffa, Matthew P. Collin, Christopher D. Buckley, Francesco Dazzi. (2009) Mesenchymal stem cells: the fibroblasts' new clothes? Haematologica 94:258-263.

[60] Pittenger et al., (1999) Multilineage Potential of Adult Human Mesenchymal Stem Cells. Science Vol. 284 no. 5411 pp. 143-147.
[61] MacFarlane et al., Anti-inflammatory role and immunomodulation of mesenchymal stem cells in systemic joint diseases: potential for treatment. Expert Opin Ther Targets. 2013 March; 17(3):243-54.
[62] Pistoia V and Raffaghello L. Unveiling the role of TNF-α in mesenchymal stromal cell-mediated immunosuppression. Eur J Immunol. 2014 February; 44(2):352-6.
[63] Bianco P, Robey P G, Simmons P J. (2008) Mesenchymal stem cells: revisiting history, concepts, and assays. *Cell Stem Cell.* 2(4):313-9.
[64] Miao Z et al., Cell Biol Int. 2006 September; 30(9): 681-7.
[65] Malek A, Bersinger N A, J Stem Cells. 2011; 6(2):75-92.
[66] Cavallo C et al., J Cell Biochem. 2011 May; 112(5): 1418-30. doi: 10.1002/jcb.23058.
[67] Shalini Vellasamy et al., World J Stem Cells. Jun. 26, 2012; 4(6): 53-61.
[68] Luan X et al., Tissue Cell. 2013 February; 45(1):32-8. doi: 10.1016/j.tice.2012.09.002. Epub 2012 Oct. 27.

What is claimed is:

1. A method of distinguishing mesenchymal stem cells (MSCs) from fibroblasts, comprising:
   isolating the MSCs from the fibroblasts using a marker EphA2 expressed on the MSCs so as to distinguish the MSCs from the fibroblasts,
   wherein the MSCs and fibroblasts are from a primary cell culture derived from placenta-related tissue.

2. The method of claim 1, wherein the placenta-related tissue is selected from the group consisting of amniotic membrane, chorionic disk, chorionic membrane, and umbilical cord.

3. The method of claim 1, wherein the isolating step is performed through an antibody-based or a nucleotide-based isolation method.

4. The method of claim 1, further comprising the preliminary steps of:
   collecting the MSCs and the fibroblasts from the placenta-related tissue;
   culturing the MSCs and the fibroblasts in a culture medium to prepare the primary culture.

5. The method of claim 3, wherein the antibody-based isolation method is an antibody-based magnetic cell sorting or an antibody-based flow cytometry.

6. The method of claim 3, wherein the nucleotide-based isolation method is a nucleotide-based flow cytometry.

7. A method of increasing a purity of mesenchymal stem cells (MSCs) population in a cell culture, comprising
   isolating and collecting MSCs using a marker EphA2 expressed on the MSCs, wherein the MSCs are from a primary culture derived from a placenta-related tissue; and
   culturing the MSCs.

8. The method of claim 7, wherein the placenta-related tissue is selected from the group consisting of amniotic membrane, chorionic disk, chorionic membrane, and umbilical cord.

9. The method of claim 7, wherein the isolating step is performed through an antibody-based or a nucleotide-based isolation method.

10. The method of claim 7, wherein the cells derived from a placenta-related tissue are cultured in a culture medium for MSC.

11. The method of claim 7, wherein the purity of the MSCs population is at least 95% at P0 after the isolating step.

12. The method of claim 9, wherein the antibody-based isolation method is an antibody-based magnetic cell sorting or an antibody-based flow cytometry.

13. The method of claim 9, wherein the nucleotide-based isolation method is a nucleotide-based flow cytometry.

14. A method of isolating a population of mesenchymal stem cells (MSCs), comprising
   isolating and collecting MSCs using a marker EphA2 expressed on the MSCs, wherein the MSCs are from a primary culture derived from a placenta-related tissue, and the population of MSCs is more responsive in an inflammatory environment.

15. The method of claim 14, wherein the isolating step is performed through an antibody-based or a nucleotide-based isolation method.

16. The method of claim 14, wherein the MSC population is more responsive to a TNF-α signaling or a TNF-α-dependent signaling.

17. The method of claim 15, wherein the antibody-based isolation method is an antibody-based magnetic cell sorting or an antibody-based flow cytometry.

18. The method of claim 15, wherein the nucleotide-based isolation method is a nucleotide-based flow cytometry.

* * * * *